United States Patent [19]

Owen et al.

[11] Patent Number: 4,801,553

[45] Date of Patent: Jan. 31, 1989

[54] METHODS OF AND APPARATUS FOR PREPARING TISSUE SPECIMENS

[76] Inventors: Stephen Owen, 8 Hillside, Royston, Herts SG8 9AY; John R. North, Browns Farmhouse, College Rd., Durrington, Salisbury SP4 8AW; Stefan Nowinski, Pearce Close, Cambridge CB3 9LY, all of United Kingdom

[21] Appl. No.: 66,377

[22] Filed: Jun. 25, 1987

[51] Int. Cl.[4] .......................... A23G 1/20; B01L 3/00; B22D 19/00; G01N 1/30
[52] U.S. Cl. ...................................... 436/174; 422/99; 422/102; 422/61; 422/58; 118/429; 425/117; 425/110; 249/83
[58] Field of Search .................. 436/174; 422/99, 102, 422/61, 58; 118/429; 425/117, 110; 249/83

[56] References Cited

U.S. PATENT DOCUMENTS

| | | | |
|---|---|---|---|
| 2,996,762 | 8/1961 | McCormick | 425/117 X |
| 3,319,289 | 5/1967 | McCormick | 425/117 |
| 3,411,185 | 11/1968 | Pickett | 249/83 |
| 3,456,300 | 7/1969 | Pickett | 425/117 |
| 3,674,396 | 7/1972 | McCormick | 425/117 |
| 3,940,219 | 2/1976 | Pickett et al. | 425/117 |
| 3,982,862 | 9/1976 | Pickett et al. | 249/83 X |
| 4,141,312 | 2/1979 | Louder et al. | 422/99 X |
| 4,557,903 | 12/1985 | McCormick | 425/117 X |

*Primary Examiner*—Barry S. Richman
*Assistant Examiner*—Amalia L. Santiago
*Attorney, Agent, or Firm*—Alan H. Spencer

[57] ABSTRACT

A cassette for holding a tissue specimen comprises a body portion (10) and a separable portion (12) which snap together to enclose a specimen (42) in a mould space (54) of the cassette. The specimen (42) is located and oriented in the mould space (54) between a compliant base portion (14) and the separable portion (12). The specimen is processed by the successive application of processing fluids before being embedded in paraffin wax. The specimen is held in its oriented position on the cassette during processing and embedding, there being no handling or re-positioning of the specimen between processing and embedding. During embedding, molten wax is supplied to a container (56) in which the cassette is placed. Wax surrounds and embeds the specimen, the container base is then cooled to solidify a base layer of wax, allowing the remaining wax to be drained from the container, leaving the wax within the cassette to solidify and cool. After removal of the cassette from the container, portions of the cassette are stripped away to leave the embedded specimen ready for microtome sectioning.

23 Claims, 9 Drawing Sheets

METHODS OF AND APPARATUS FOR PREPARING TISSUE SPECIMENS

FIELD OF THE INVENTION

This invention relates to methods of and apparatus for preparing tissue specimens for microtome sectioning.

BACKGROUND TO THE INVENTION

Conventionally, tissue specimens are prepared for microtome sectioning in two sequential stages. In the first stage, the tissue specimen is placed in a cassette and processed by solvents which remove the water content of the specimen. The specimen is removed from the cassette and subjected to the second stage, called embedding, which involves placing the specimen in a small dish which is then filled with molten wax. This wax impregnates and surrounds the specimen which is thus embedded in wax. The embedded specimen is then removed from the dish and the wax block is mounted in the clamp of a microtome for sectioning of the specimen. It is important that the specimen is accurately positioned in the dish prior to the wax setting around the specimen, so that sectioning of the specimen occurs along the appropriate planes to reveal the desired cell structure. In the past, this positioning has been achieved by allowing a few drops of molten wax to fall into the base of the otherwise empty dish, allowing the resulting small quantity of wax partially to set and to position the specimen in the plastic wax in the desired orientation using tweezers. This holds the specimen in the required position, after which more molten wax is added to the container, to fully embed the specimen.

In one aspect the invention aims to provide a cassette, and a method of using a cassette, wherein a tissue specimen can be accurately and precisely located and oriented in the cassette prior to embedding of the cassette in the embedding medium.

In another aspect the invention is concerned with embedding a plurality of specimens simultaneously in a container. Hitherto this has been done by placing the cassettes in a container into which molten wax is introduced to a depth sufficient to cover the cassettes. The wax is then caused or allowed to cool, but the problem of removal of the cassettes from the solidified block of wax then presents itself.

SUMMARY OF THE INVENTION

According to one aspect of the invention there is provided a method of preparing a tissue specimen for microtome sectioning, comprising locating the specimen between a base portion and a separable portion of a cassette so that the specimen is held in a desired orientation in the cassette, embedding the located specimen in an embedding medium and removing the separable portion of the cassette to leave the located and embedded specimen supported on the base portion of the cassette for subsequent microtome sectioning of the specimen. Hence, in this aspect of the invention the specimen is held in a desired orientation in the cassette prior to embedding. This can conveniently be achieved by orienting the specimen in the cassette by the use of tweezers prior to the specimen being held and positively located in the desired orientation in the cassette. Preferably, the base portion and separable portion are brought together and interengaged, with the tissue specimen held and located between them. To aid this retention and location, the specimen is preferably resiliently held between the base portion and the separable portion as a result of the base portion being compliant. This compliance has the advantage that any shrinkage of the specimen is then compensated for automatically.

As a further aid to location and retention of the tissue specimen, the base portion may be recessed or dished in order to receive and locate the tissue specimen with a cradling action.

According to another aspect of the invention there is provided a cassette for holding a tissue specimen, comprising a body portion and a separable portion which interengage to define between them a space for accommodating the located tissue specimen so that the latter is held in a desired orientation in the cassette, the cassette having apertures which render the space fluid permeable, the cassette also serving as a mould for an embedding medium which fills the space and embeds the located tissue specimen, the separable portion of the cassette being removable to leave the located and embedded specimen supported on a base portion of the body portion of the cassette for subsequent microtome sectioning of the specimen.

The base portion is preferably rectangular and may, as previously mentioned, be compliant. This is preferably achieved by resilient linkage means which may include four parts, each part interconnecting a corresponding one of four sides of the base portion with an adjacent side of the remainder of the body portion, each part of the resilient linkage means having three sets of hinges and two plates, one set of hinges interconnecting the base portion and a first plate, a second set of hinges interconnecting the first plate and a second plate and a third set of hinges interconnecting the second plate and the adjacent side of the remainder of the body portion, the linkage means constraining the base portion to remain substantially parallel with the separable portion. This parallelism of the base portion and the separable portion avoids any tendency for the tissue specimen to be squeezed asymmetrically or moved towards one side of the cassette.

According to a further aspect of the invention there is provided apparatus for simultaneously embedding a plurality of specimens, which comprises a container, a heat-conducting bottom in said container, supply means for delivering a quantity of a melted embedding medium into said container, chilling means for cooling said bottom below the medium melting point, and outlet means for draining surplus medium, in combination with a plurality of one-time moulds temporarily positioned on said bottom.

Preferably, each one-time mould is constituted by a cassette according to said another aspect of the invention.

According to a yet further aspect of the invention there is provided apparatus for simultaneously embedding a plurality of tissue specimens individually and in one-time moulds, each of the moulds having a vertical mould wall defining a mould area, an open bottom, and a perforated specimen-orientation means in the mould area, which comprises a container, a heat-conducting bottom in said container, supply means for delivering a quantity of a melted embedding medium into said container, chilling means for cooling said bottom below the medium melting point, and outlet means for draining surplus melted medium from said container, whereby the specimen in each mould can be embedded by placing the plurality of the moulds on the container bottom; introducing the quantity of embedding medium; chilling a bottom layer of the embedding medium; draining the unchilled embedding medium from around the moulds and allowing the embedding medium in the moulds to solidify before removal of the moulds from the container.

According to a yet further aspect of the invention there is provided a method of simultaneously embedding a plurality of specimens, comprising supplying molten embedding medium to a container, allowing the embedding medium to surround specimens located in respective cassettes supported on a base of the container, chilling the base of the container to seal the junction between the base of the container and each cassette against the egress of embedding medium from the cassette, draining the embedding medium from the container to leave the embedding medium within each cassette, and separating each cassette from the base of the container to provide an embedded specimen for subsequent microtome sectioning.

The invention will now be further described by way of example with reference to the accompanying drawings in which:

FIG. 1 is a perspective view of a cassette according to the invention with parts broken away to show internal detail, FIG. 2 is a longitudinal sectional view of a body portion of the cassette, FIG. 3 is a transverse sectional view of the body portion of the cassette, FIG. 4 is an underside plan view of the body portion of the cassette, FIG. 5 is a plan view of a separable portion of the cassette, FIG. 6 is a perspective view of a container used in embedding the cassette, FIG. 7 is a diagrammatic sectional view through the container of FIG. 6, FIG. 8 is an underside plan view of the container of FIGS. 6 and 7, and FIGS. 9a to 9l are a series of views showing stages in the use of the cassette.

DETAILED DESCRIPTION OF THE DRAWINGS

Figure 1:
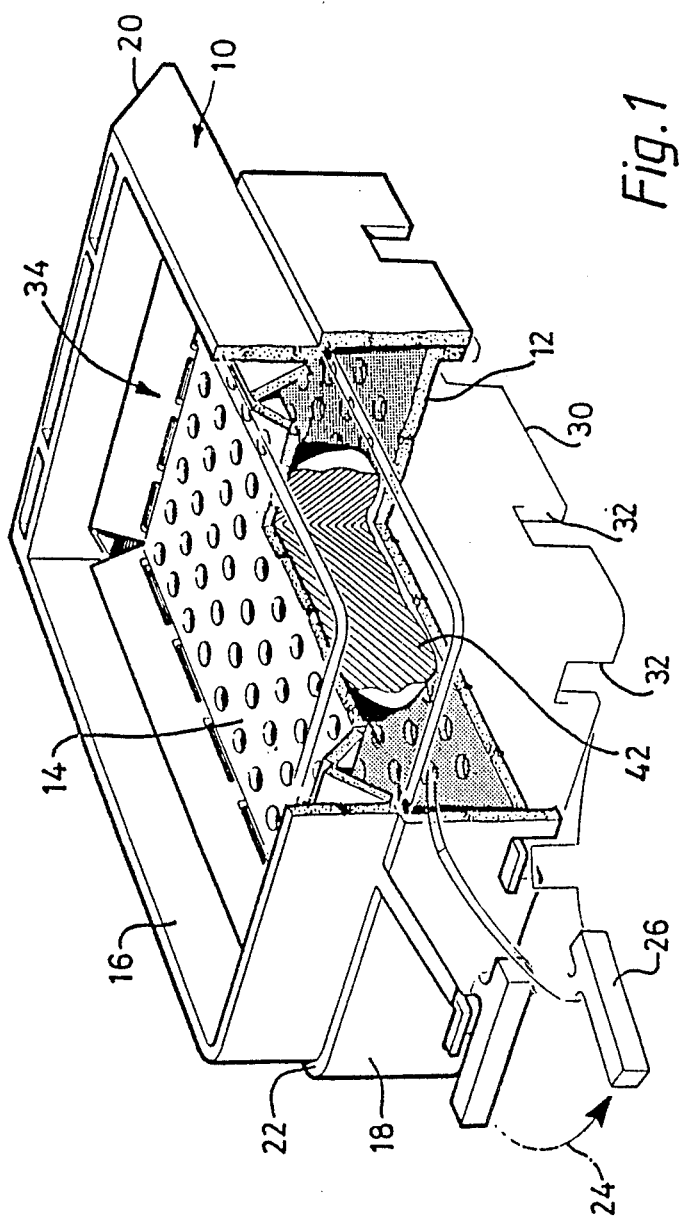

The cassette comprises a body portion 10 and a separable portion 12. FIG. 1 shows the body portion 10 and the separable portion 12 in operative engagement, FIGS. 2, 3 and 4 show the body portion 10 alone and FIG. 5 shows the separable portion 12 alone.

The body portion 10 has a perforated base portion 14 in the form of a rectangular panel surrounded by an upwardly projecting peripheral wall 16 and a downwardly projecting wall 18. At one end of the body portion 10, the upwardly projecting peripheral wall 16 forms an angled face 20 on which identifying matter can be written. The upwardly and downwardly projecting walls 16 and 18 adjoin along a step 22, the line of the step 22 being formed as a line of weakness so that the lower peripheral wall 18 can be separated from the remainder of the body portion by tearing along the line of weakness, as indicated by the arrow 24 in FIG. 1. The downwardly projecting peripheral wall 18 has an integrally formed projecting tab 26 which is gripped and pulled to separate the wall 18 from the remainder of the body portion 10. The lower edge 30 of the wall 18 has rectangular notches 32, three in each side, imparting a castellated appearance to the lower edge 30.

Figure 2:
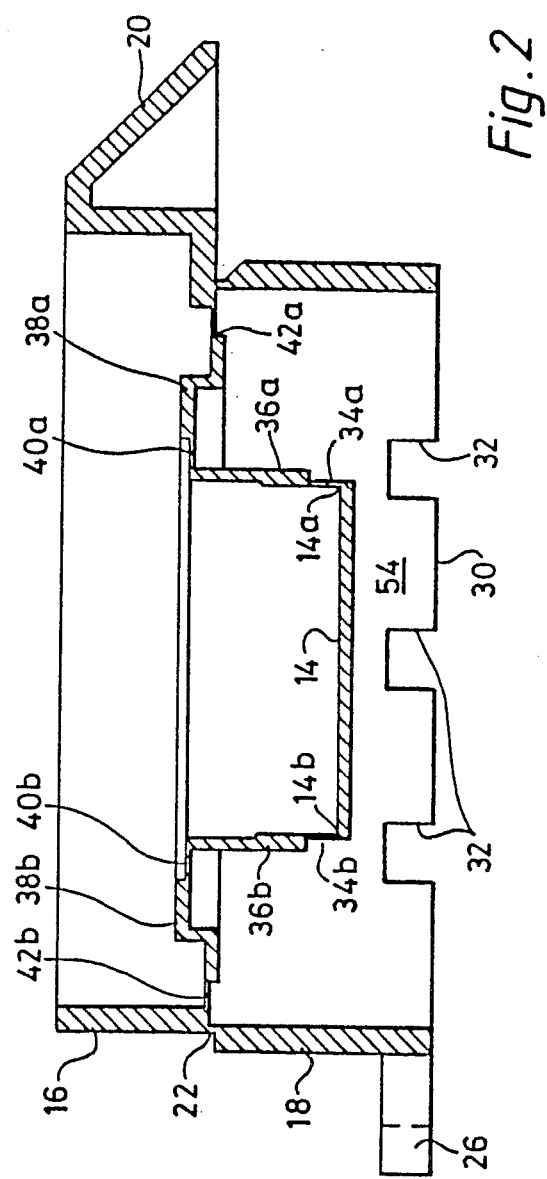
Figure 3:
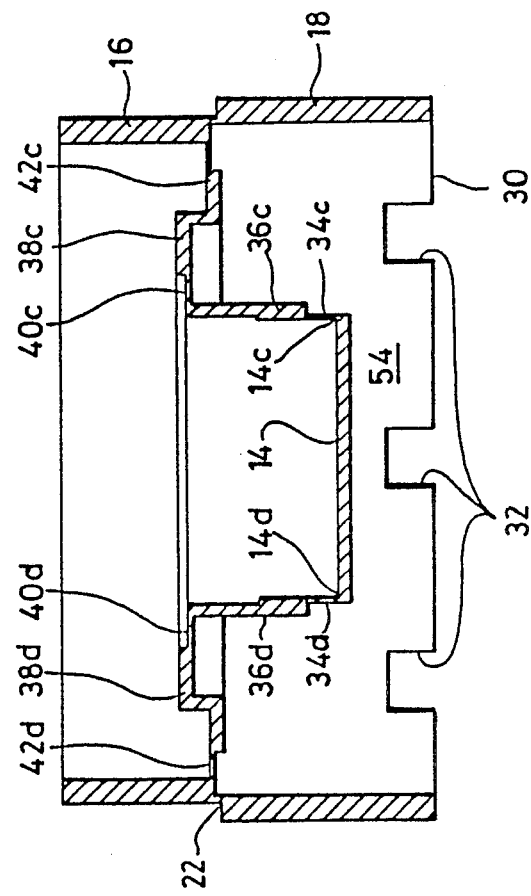
Figure 4:
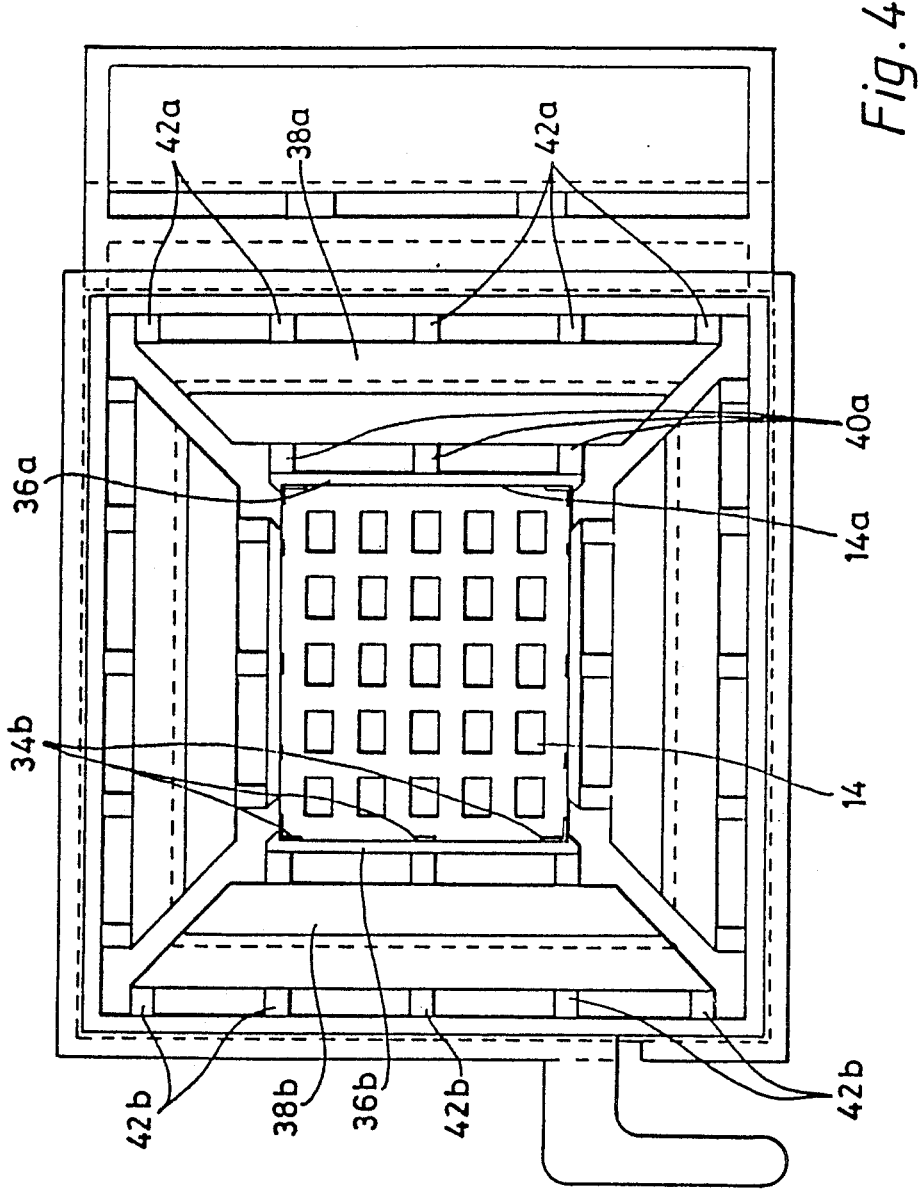
Figure 5:
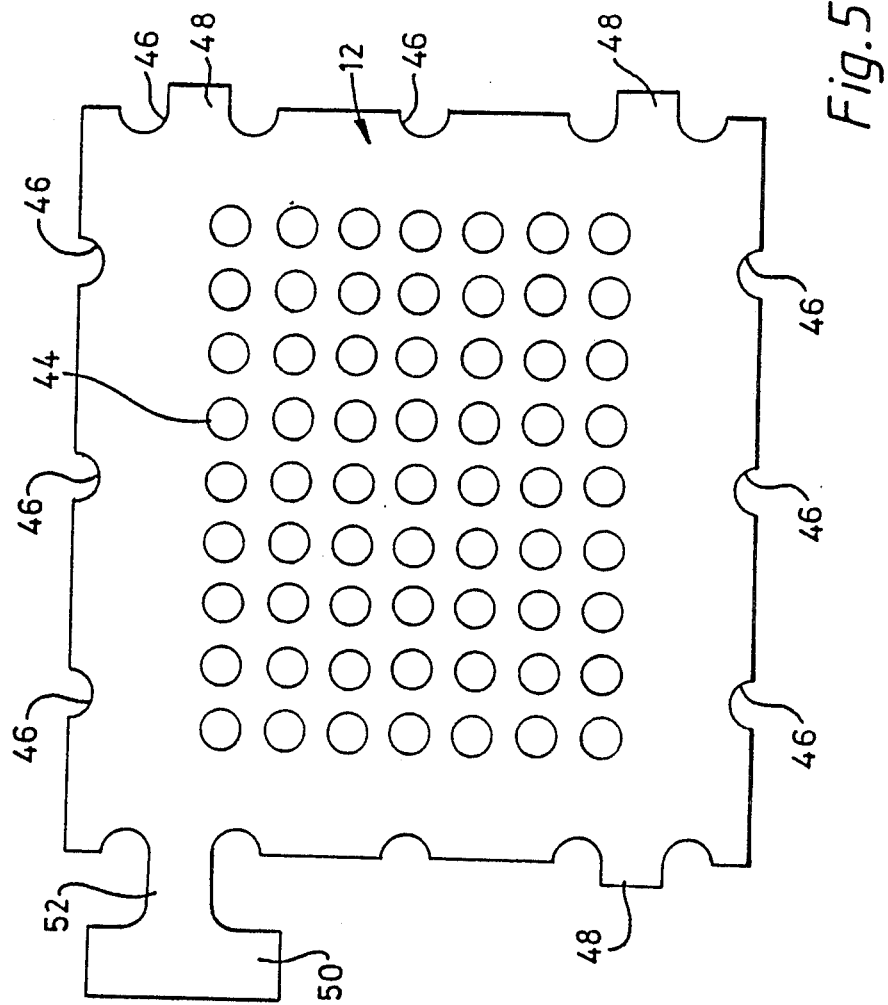

The base portion 14 is connected to the remainder of the body portion 10 by linkage means 34, the whole structure of the body portion of FIGS. 2 to 4 being integrally moulded from a synthetic plastics material. The linkage means 34 are in four parts, respectively connecting the four edges of the rectangular base portion 14 to the adjacent length of the step 22. For example, referring to FIGS. 2 and 4, one side 14a of the body portion 14 is connected by a first hinge 34a to a first plate 36a which is in turn connected to a second plate 38a by a second hinge 40a. The second plate 38a is connected to the adjacent length of the step 22 by a third hinge 42a. The opposite side 14b of the base portion 14 is connected to the adjacent length of the step 22 by a similar series of three hinges 34b, 40b and 42b and two plates 36b and 38b. Referring to FIGS. 3 and 4, the two remaining sides 14c and 14d are connected to adjacent lengths of the step 22 by respective hinges and plates, namely three hinges 34c, 40c and 42c and two plates 36c and 38c; and three hinges 34d, 40d and 42d and two plates 36d and 38d.

The linkage means 34 provide the base portion 14 with a degree of compliance which enables it to move with a resilient action with respect to the surrounding walls 16 and 18. FIGS. 2 and 3 show the base portion in its normal undeflected condition, and FIG. 1 shows the base portion in a displaced operative condition in which the base portion 14 has moved upwardly with respect to the walls 16 and 18 in order to accommodate a tissue specimen 42 located between the base portion 14 and the separable portion 12. The linkage means 34 has compliance sufficient to prevent distortion of the specimen 42 and stiffness sufficient to hold and retain the specimen 42 in the cassette.

As best seen in FIG. 4, each hinge 34a, 34b, 34c, 34d, 40a, 40b, 40c, 40d consists of three hinge elements; each hinge 42a, 42b, 42c, 42d consists of five hinge elements.

The separable portion 12 of the cassette shown in FIG. 5 comprises a generally rectangular panel of plastic material having a rectangular perforated area 44. Each longer edge of the separable portion 12 has three semicircular recesses 46, one shorter edge has five recesses 46 and two projecting lugs 48, and the other shorter edge has five recesses 46, a projecting tab 50 and a single lug 48. The separable portion 12 engages with the body portion 10 with a snap action, this occurring as a result of the separable portion 12 being pressed into the wall 18, as shown in FIG. 1. In this condition the three lugs 48 of the separable portion 12 engage in corresponding notches 32, as does the neck 52 of the tab 50. When the body portion 10 and separable portion 12 are interengaged the circular recesses 46 register with corresponding notches 32 so as to define passages extending from outside the cassette into the mould space 54 defined between the base portion 14 and the separable portion 12.

As will be subsequently explained in detail, the specimen 42 is located and oriented in a desired position between the resilient base portion 14 and the separable portion 12 which is snapped into position to hold the specimen 42 in its oriented and located position in the cassette. The specimen is then processed in a conventional manner so as to remove water from the specimen, this being done by the successive application of processing fluids. During processing, the specimen may shrink and any such shrinkage is taken up automatically by the compliance of the base portion 14, without altering the retention or orientation of the specimen 42.

Figure 6:
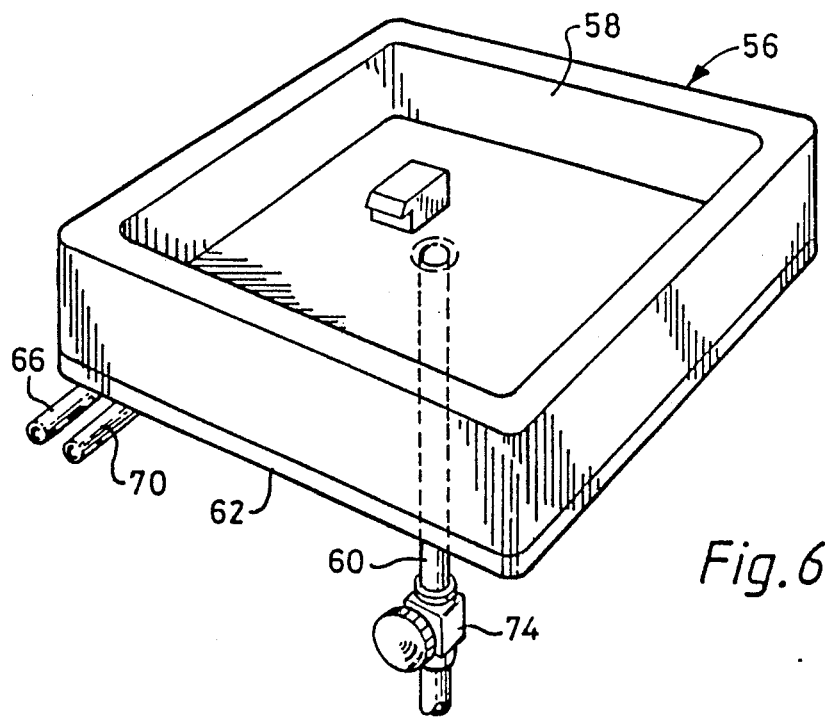
Figure 7:
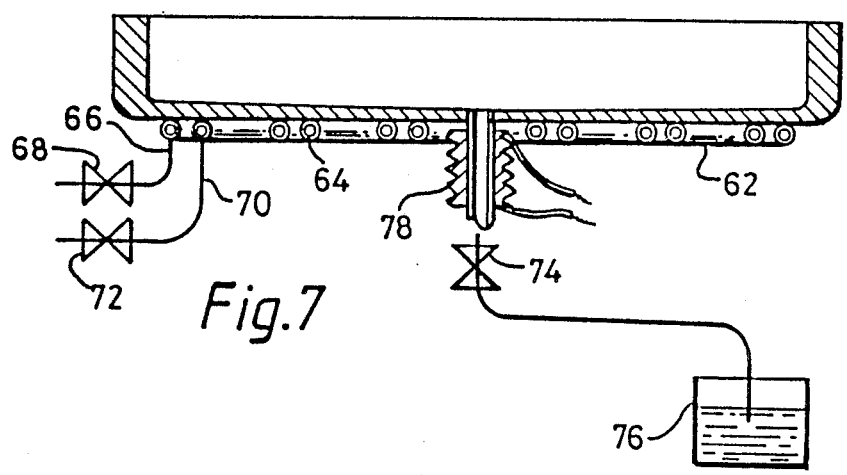
Figure 8:
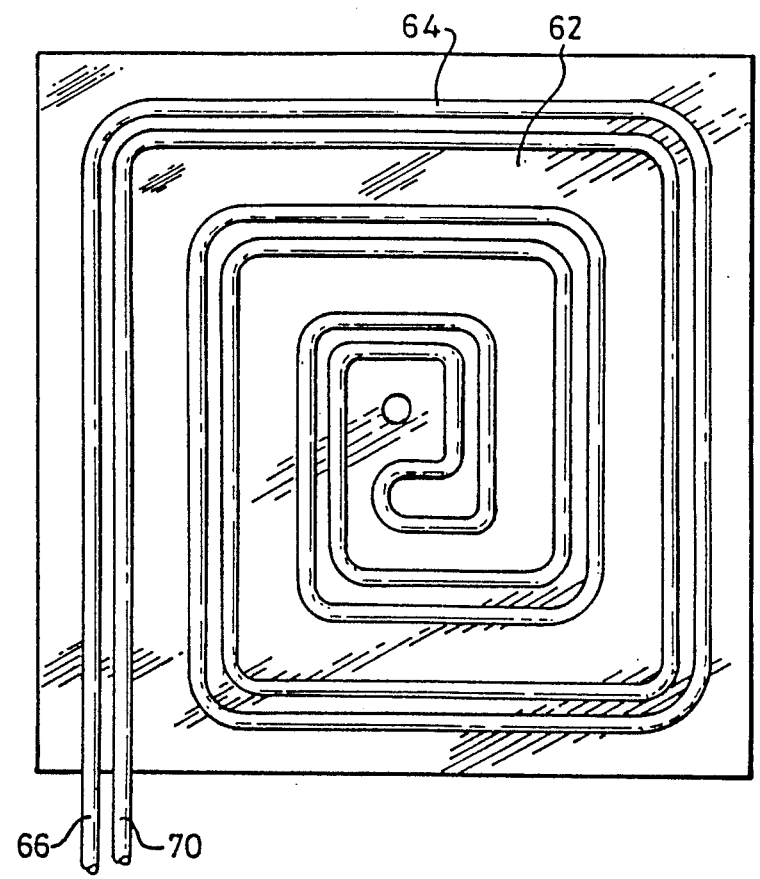

Having been processed, the specimen is then embedded in paraffin wax by use of the apparatus shown in FIGS. 6 to 8. The embedding apparatus comprises a container 56 with upstanding walls 58 and a central pipe 60 through which molten wax is supplied to and drained from the container 56. The container 56 has a heat conducting bottom 62 below which is arranged a coiled tube 64 for the passage of heating fluid or cooling fluid, for example hot or cold water respectively. The tube 64 has an inlet 66 with an inlet valve 68, and an outlet 70 with an outlet valve 72. The pipe 60 communicates with a wax control valve 74 which leads to a reservoir of wax indicated diagrammatically at 76. The reservoir 76 is placed under pressure to feed molten wax through the open valve 74, upwardly through the pipe 60 and into the container 56. The source 76 is partially evacuated to drain surplus molten wax from the container 56. The pipe 60 is surrounded by heating tape 78 which is electrically energised to maintain the central area of the base of the container warm even when cooling fluid is passing through the tube 64.

Figure 9A:
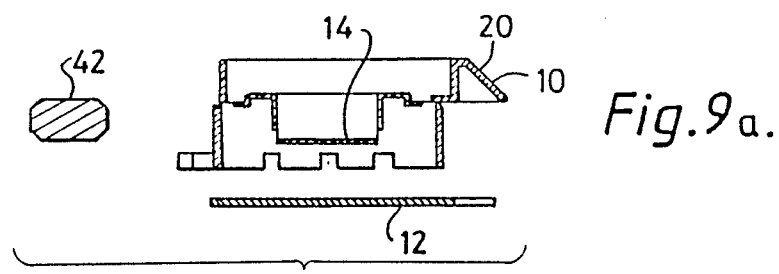
Figure 9B:
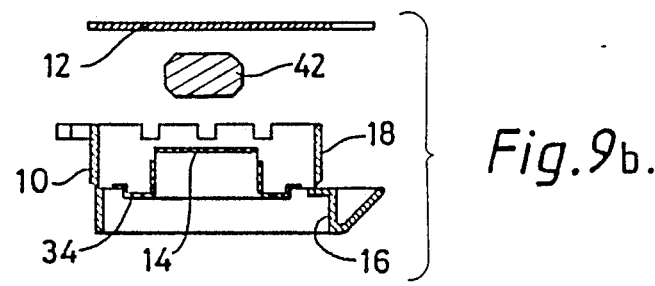
Figure 9C:
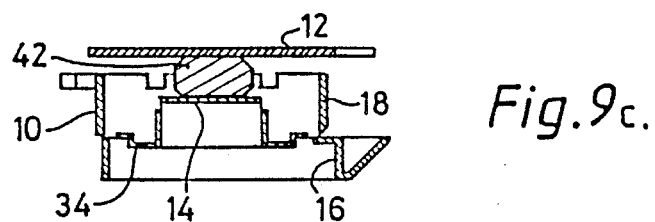
Figure 9D:
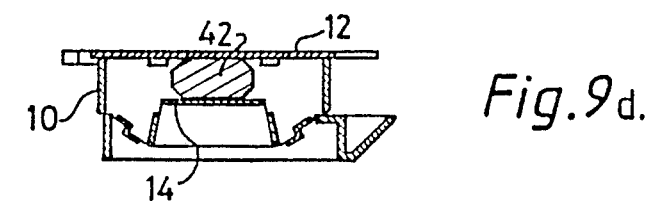

A representative sequence of operations will now be described with reference to FIG. 9. FIG. 9a shows the specimen 42 ready to be loaded in the cassette which at this stage comprises the separate portions 10 and 12. At this stage the specimen 42 is identified by an appropriate marking on the angled face 20. The body portion 10 is then inverted (FIG. 9b) ready for loading of the specimen 42 in the cassette. The specimen 42 is loaded into the cassette by locating the specimen 42 between the base portion 14 and the separable portion 12 (FIG. 9c). The separable portion 12 is snapped into position on the body portion 10 by interengagement of the lugs 48 and neck 52 in the corresponding notches 32 (FIG. 9d), whereby the separable portion 12 is brought into a predetermined position with respect to the wall 18. In this operation, care is taken to ensure that the specimen 42 is in the desired orientation in the cassette.

Figure 9E:
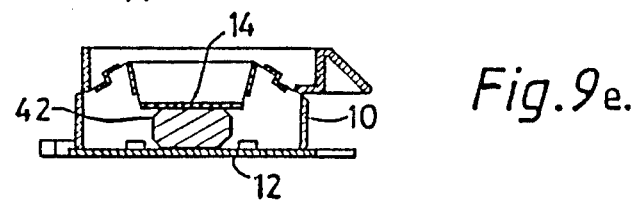

As the separable portion 12 is pressed into position on the wall 18 of the body portion 10, the compliant base portion 14 moves as a result of flexure of the linkage means 34. The arrangement of the linkage means is such that the base portion 14 remains parallel with the separable portion 12, the degree of compliant movement of the base portion 14 depending on the size of the specimen 42. The loaded cassette is inverted and is now ready for processing (FIG. 9e). The linkage means do not project above the upper edge of the wall 16, regardless of the size of the specimen.

Figure 9F:
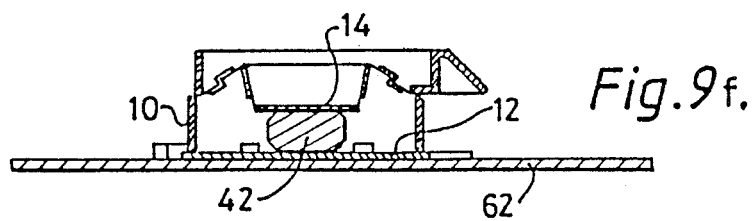
Figure 9G:
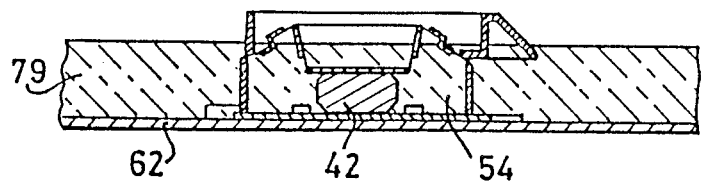
Figure 9H:
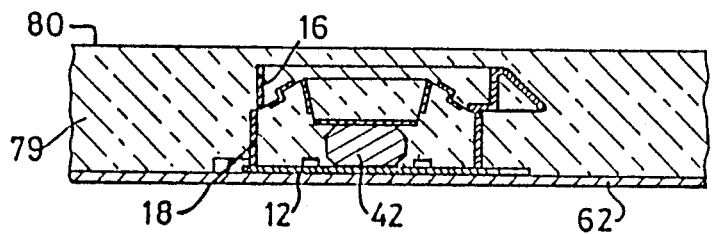

The specimen 42 may be processed in the same container 56 as is used for embedding, in which case the cassette and sample are placed in the container 56 which would then have a cover to enable processing fluids to be successively delivered to the container in order to process the specimen 42 in a known manner. Having been processed, the specimen 42 is now ready to be embedded. The cassette carrying the located and processed specimen 42 is placed in the container 56 so that the edge 30 of the cassette rests on the bottom 62 of the container 56 (FIG. 9f). In practice, a number of such loaded cassettes would be placed in a single layer in the container 56 so that a number of specimens can be embedded simultaneously. If desired conventional cassettes can be placed on the single layer of inventive cassettes and embedded in the same operation.

Molten paraffin wax 79 (FIG. 9g) is supplied to the container 56 through the pipe 60. The molten paraffin wax flows upwardly into the mold space 54 through the passages defined by the recesses 46 and the notches 32. The wax is kept molten by hot fluid being passed through the tube 64 below the heat conducting bottom 62 of the container 56. The supply of wax 79 continues until the level 80 of molten wax is above the level of the upper edge of the wall 16 of the body portion 10.

Figure 9I:
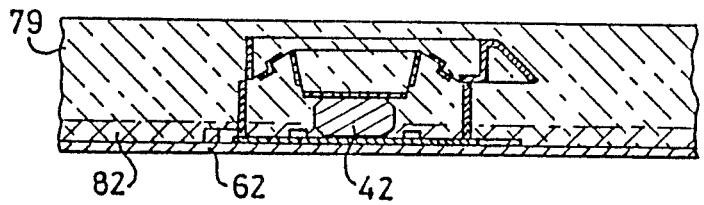

By appropriate change-over of the valves 68 and 72, cooling fluid is passed through the tube 64 and this has the effect of solidifying a base layer 82 of the wax as shown in FIG. 9i. Cooling of the bottom 62 of the container 56 is continued until the base layer 82 is sufficiently deep to seal the passages formed by the notches 32 and the recesses 46. As a result, the base layer 82 seals the base of the cassette to the container bottom 62.

Figure 9J:
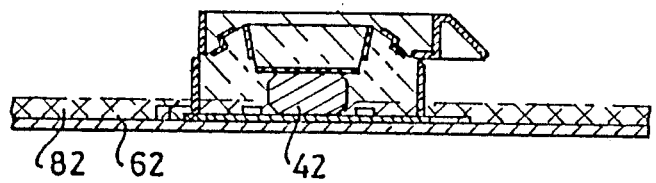

Excess molten wax is now drained from the container 56 by applying suction to the source 76 and opening the valve 74 (FIG. 9j). During this stage the heating tape 78 is energised to prevent solidification of wax around the central pipe 60. Because the layer 82 seals the base of the cassette to the bottom 62 of the container 56, the wax is retained in the cassette, the wax then being allowed to cool and solidify, which causes a certain degree of contraction indicated at 84 in FIG. 9k. The specimen 42 is now embedded in solidified wax and the complete cassette with the embedded specimen 42 is removed from the container, either by cutting around the wax or by temporarily heating the base 62 is order to cause localised melting of the wax to facilitate release of the cassette from the bottom 62 of the container 56.

Figure 9K:
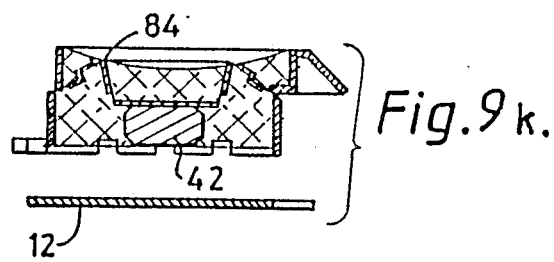
Figure 9L:
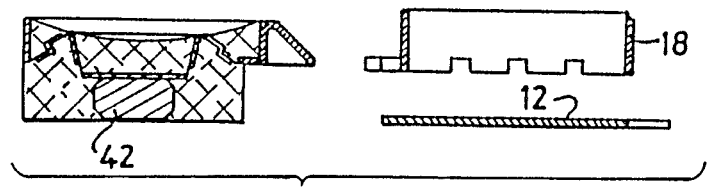

The separable portion 12 is now removed from the wall 18 by grasping the projecting tab 50 and pulling the portion 12 away from the body portion 10 (FIG. 9k). The wall 18 is then removed by grasping the projecting tab 26 and separating the wall 18 by tearing along the line of weakness defined by the step 22. The embedded specimen 42, located in the remaining portion of the cassette, is now ready for microtome sectioning, the base portion 12 and the torn away wall 18 being discarded (FIG. 9l). It will be appreciated that the wall 16 provides two accurately spaced parallel surfaces for accurate and reliable location of the embedded cassette in the microtome machine. It will also be appreciated that the specimen 42, having been initially located and oriented between the base portion 14 and the separable portion 12 has not been moved, adjusted or directly handled in any way, with the result that the specimen 42 is embedded in its desired location.

The cassette may have an opening to allow for the insertion of a pair of tweezers for accurately positioning the specimen during closure of the separable portion 12 and the body portion 10. Also, the base portion 14 may be shaped, eg with a recess, to aid central location of the specimen 42 in the mould space 54. Instead of being paraffin wax, the embedding medium may be a plastic material, eg epoxy.

In a modified form of the cassette (not illustrated) the separable portion 12 pushes into the wall 18 to an extent dependent on the size of the specimen. The wall 18 and the separable portion 12 engage with a ratchet-like action as the separable portion is pushed into position with the specimen located between the separable portion 12 and the base portion 14 which in this case is not compliant.

After embedding, the wall 18 is removed before the separable portion is stripped away from the solidified wax, leaving the embedded specimen supported on the remainder of the body portion of the cassette, ready for clamping in a microtome for sectioning.

We claim:

1. A method of preparing a tissue specimen for microtome sectioning, comprising the steps of locating the specimen between a base portion and a separable portion of a cassette connected at an interface, resiliently holding the specimen in a desired orientation in the cassette, processing the located specimen in at least one fluid while holding the specimen in the desired orientation, embedding the processed and located specimen in the cassette in an embedding medium and removing the separable portion of the cassette to leave the located and embedded specimen supported on the base portion of the cassette in the desired orientation for subsequent microtome sectioning of the specimen.

2. A method according to claim 1, wherein, after embedding, a wall of the cassette is removed to facilitate separating the separable portion of the cassette from the embedding medium.

3. A method according to claim 1, wherein the separable portion of the cassette is separated from the embedding medium, a wall of the cassette is parted along an interface and removed to leave the embedded specimen in the desired orientation and ready for microtome sectioning.

4. A method according to claim 1, wherein the base portion is compliant and maintains the specimen orientation by taking up any shrinkage of the specimen.

5. A method according to claim 4, wherein the separable portion and the wall interengage to locate the separable portion in a predetermined position with respect to the wall, a projection on the separable portion extending beyond the wall to ease parting of the separable portion from the embedding medium and the wall.

6. A method according to claim 1, wherein the embedding step comprises placing the cassette holding the specimen in the desired orientation on a container bottom and introducing the embedding medium in a liquid condition into the container so that the embedding medium enters the region between the base portion and the separable portion of the cassette through passages below the separable portion and then through perforations in the separable portion in order to surround the located specimen.

7. A method according to claim 6, wherein a plurality of cassettes are supported in the container in a single layer on the bottom thereof.

8. A method according to claim 6, wherein the embedding step further includes cooling the container bottom after introduction of the embedding medium, solidifying a layer of embedding medium to seal the passages, draining excess embedding medium from the container leaving the embedding medium within the cassette.

9. A method according to claim 8, wherein the bottom of the container is heated to facilitate release of the cassette from the container bottom after excess embedding medium has been drained.

10. A method according to claim 8, wherein the embedding medium is paraffin wax.

11. A method according to claim 10, further including the step of permitting the wax in the cassette to cool to a solid before the cassette is separated from the container bottom.

12. A cassette for holding a tissue specimen, comprising a body portion and a separable portion, means to interengage said body and separable portions to define between said portions a space, a base portion, means resiliently connecting said base portion to the body portion for holding a tissue specimen in a desired orientation in the cassette, said separable and base portions having apertures rendering the space fluid permeable, the cassette also serving as a mould for an embedding medium which fills the space and embeds a so located tissue specimen, the separable portion of the cassette being removable to leave a so located and embedded specimen supported on said base and body portions of the cassette for subsequent microtome sectioning of the specimen.

13. A cassette according to claim 12, wherein said body portion includes a removable wall and said interengagement means interengages said separable portion with said removable wall.

14. A cassette according to claim 12, wherein said connection means includes a plurality of compliant hinges connecting said base portion to said body portion and wherein said base portion, said body portion and said hinges are integrally molded as one piece.

15. A cassette according to claim 12, wherein said interengagement means provides a predetermined position of the separable portion with respect to the base portion.

16. A cassette according to claim 15, wherein the body portion has a projecting tab to facilitate removal of a downwardly projecting peripheral wall of said body portion.

17. A cassette according to claim 12, wherein said body portion is rectangular in cross-section and said base portion is rectangular and each has four edges, four resilient connecting means, each connecting means having a hinge connecting one of said four edges of said body portion to one edge of a first plate, a second hinge connecting the other edge of the first plate to one edge of a second plate and a third hinge connecting the other edge of the second plate to a respective one of the edges of said base portion, whereby the base portion is maintained parallel to the separable portion.

18. A cassette according to claim 17, wherein the body portion, base portion and connecting means are integrally moulded in one piece from a synthetic plastic material.

19. A cassette for holding a tissue specimen, comprising a body portion having a perforated base portion surrounded by an upwardly projecting peripheral wall and a downwardly projecting peripheral wall, and a separable portion in the form of a perforated panel, the separable portion and the downwardly projecting peripheral wall having interengageable formations which enable the separable portion and the base portion to be brought together with the tissue specimen located between the base portion and the separable portion, a plurality of notches being spaced around the lower edge of the downwardly projecting peripheral wall to provide an entry for hot embedding medium and preventing drainage of embedding medium from the cassette when a lower layer of the embedding medium is solidified, the downwardly projecting peripheral wall being separable from the base portion along a line of weakness, so that after the tissue specimen located in the cassette has been processed and then embedded with an embedding medium the separable portion and the peripheral wall are removed to leave the embedded specimen supported on the base portion for microtome sectioning.

20. A cassette according to claim 17, wherein the notches are rectangular, imparting a castellated shape to the lower edge of the peripheral wall.

21. Apparatus for simultaneously embedding a plurality of specimens, which comprise a container, a heat-conducting bottom in said container, supply means for delivering a quantity of a melted embedding medium into said container, chilling means for cooling said bottom below the medium melting point thereby providing a solidified layer of embedding medium, and outlet means for draining surplus medium, in combination with a plurality of one-time moulds temporarily positioned on said bottom, each of said one-time moulds has a peripheral wall surrounding a space for accommodating the specimen and said peripheral wall cooperates with said bottom to form passages whereby melted embedding medium enters each of said one-time moulds through said passages and said solidified layer blocks, said passages trapping the remaining melted embedding medium in said mould, when the surplus embedding medium is drained.

22. Apparatus according to claim 21, wherein the supply means and the outlet means include a pipe leading through the bottom of the container, the embedding medium being supplied upwardly through the pipe and surplus medium draining downwardly through the pipe.

23. Apparatus according to claim 21, wherein the chilling means comprises a tube for the passage of a cooling medium for cooling said bottom, or the passage of a heating medium for heating said bottom.

* * * * *